(12) United States Patent
Lu et al.

(10) Patent No.: US 10,605,741 B2
(45) Date of Patent: Mar. 31, 2020

(54) ACCURATE COLORIMETRIC BASED TEST STRIP READER SYSTEM

(71) Applicant: International Business Machines Corporation, Armonk, NY (US)

(72) Inventors: Minhua Lu, Mohegan Lake, NY (US); Vince Siu, Thornhill (CA); Russell Budd, North Salem, NY (US); Evan Colgan, Montvale, NJ (US); John Knickerbocker, Monroe, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/022,282

(22) Filed: Jun. 28, 2018

(65) Prior Publication Data

US 2020/0003698 A1   Jan. 2, 2020

(51) Int. Cl.
*G01N 21/80* (2006.01)
*G06T 7/90* (2017.01)
*H04N 5/225* (2006.01)
*G06K 9/46* (2006.01)

(52) U.S. Cl.
CPC .......... *G01N 21/80* (2013.01); *G06K 9/4647* (2013.01); *G06T 7/90* (2017.01); *H04N 5/2256* (2013.01); *G01N 2201/0627* (2013.01); *G01N 2201/127* (2013.01); *G06T 2207/10152* (2013.01)

(58) Field of Classification Search
CPC .......... G01N 21/80; G01N 2201/0627; G01N 2201/127; G06T 7/90; G06T 2207/10152; G06K 9/4647; H04N 5/2256
See application file for complete search history.

(56) References Cited

U.S. PATENT DOCUMENTS

| 6,394,952 | B1 | 5/2002 | Anderson et al. |
| 9,778,200 | B2 | 10/2017 | Tsai et al. |
| 2013/0203043 | A1 | 8/2013 | Ozcan et al. |
| 2014/0170757 | A1 | 6/2014 | Tsai et al. |
| 2014/0240491 | A1 | 8/2014 | Kauniskangas et al. |

(Continued)

FOREIGN PATENT DOCUMENTS

| CN | 104215757 A | 12/2014 |
| CN | 104964973 A | 10/2015 |

OTHER PUBLICATIONS

Simerville et al. "Urinalysis: A Comprehensive Review," American Family Physician, vol. 71, No. 6, pp. 1153-1162 (Mar. 2005).

(Continued)

*Primary Examiner* — Huy T Nguyen
(74) *Attorney, Agent, or Firm* — Kristofer Haggerty; Michael J. Chang, LLC

(57) ABSTRACT

Techniques for colorimetric based test strip analysis and reader system are provided. In one aspect, a method of test strip analysis includes: illuminating a test strip wetted with a sample with select spectrums of light, wherein the test strip includes test pads that are configured to change color in the presence of an analyte in the sample; obtaining at least one digital image of the test strip; and analyzing color intensity from the at least one digital image against calibration curves to determine an analyte concentration in the sample with correction for one or more interference substances in the sample that affect the color intensity. A calibration method and a reader device are also provided.

21 Claims, 9 Drawing Sheets

(56) References Cited

U.S. PATENT DOCUMENTS

| | | | |
|---|---|---|---|
| 2014/0301898 A1 | 10/2014 | Phelan | |
| 2015/0254845 A1* | 9/2015 | Tsai | G01N 21/78 |
| | | | 382/128 |
| 2015/0308961 A1 | 10/2015 | Burg et al. | |
| 2016/0048739 A1 | 2/2016 | Burg | |
| 2016/0080548 A1* | 3/2016 | Erickson | H04M 1/72527 |
| | | | 455/556.1 |
| 2017/0026620 A1 | 1/2017 | Kalambur et al. | |
| 2017/0154438 A1 | 6/2017 | Kisner et al. | |
| 2017/0329120 A1* | 11/2017 | Hsu | G02B 21/362 |
| 2018/0017498 A1 | 1/2018 | Tsai et al. | |
| 2018/0089532 A1 | 3/2018 | Xu | |
| 2018/0107790 A1* | 4/2018 | Pulitzer | G16H 10/40 |

OTHER PUBLICATIONS

Lee et al., "A Low-Cost, High-Performance System for Fluorescence Lateral Flow Assays," Biosensors Oct. 2013, 3(4), 360-373.
English Abstract of CN104964973A by Deng Shuangsheng et al., Oct. 7, 2015 (1 page).

* cited by examiner

| Interference parameters | Measurement impacted |
|---|---|
| pH | Nitrite, Protein, Specific gravity |
| Specific gravity | Nitrite, Glucose, blood, leucocyte |
| Nitrite | Urobilinogen |
| Urobilinogen | Nitrite |
FIG. 2
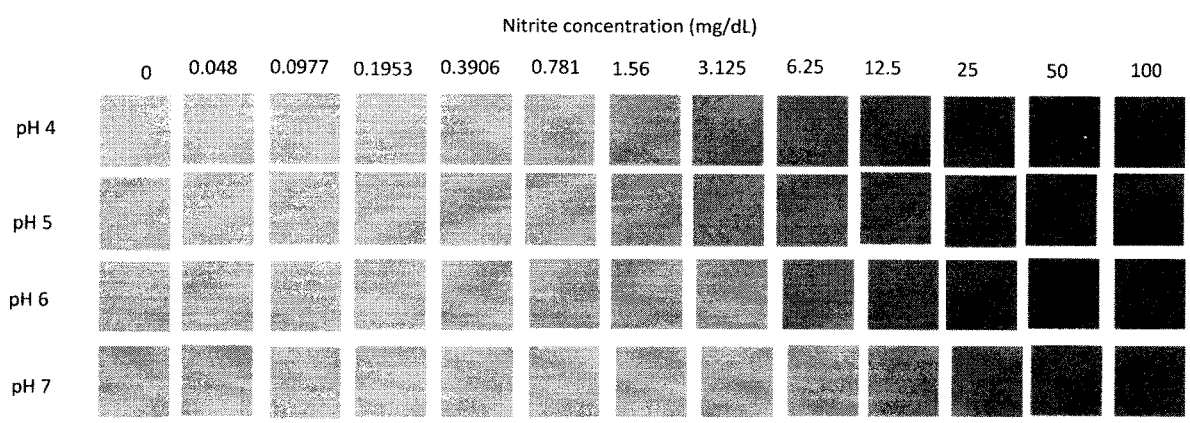
FIG. 3
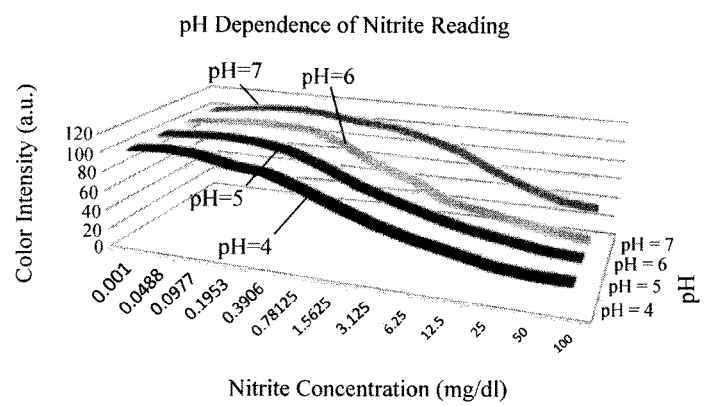
FIG. 4

500

Nitrite Concentration for pad w/color intensity of 91%

| pH value | Nitrite Concentration (mg/dl) |
|----------|-------------------------------|
| 4        | 0.19                          |
| 5        | 0.4                           |
| 6        | 0.78                          |
| 7        | 3.125                         |

ACCURATE COLORIMETRIC BASED TEST STRIP READER SYSTEM

FIELD OF THE INVENTION

The present invention relates to test strips analysis, and more particularly, to improved colorimetric based test strip analysis and reader system.

BACKGROUND OF THE INVENTION

Fluid sample testing often involves contacting a test strip with the sample, whereby the test strip contains reactants for one or more analytes. Test strips are commercially available for a variety of analytes such as blood glucose, pH, biomarkers, etc. For instance, a well-known test strip provider is Becton, Dickinson and Company, Franklin Lakes, N.J. Reaction of the analytes with the reactants on the test strip effects a color change that can then be detected using a reader. An example of commercially-available test strip readers includes those from Roche Diagnostics, Indianapolis, Ind.

A drawback to conventional test strip readers is that they are highly subjective and prone to errors. Namely, variations in factors such as sample volume, reaction time, the light source or sources used to illuminate the sample for reading, etc. can all produce a different color reading. Thus, these conventional tests are highly subjective and prone to errors. In fact, when tested against a panel of test strips with known concentrations of analytes, conventional readers produced a significant number of errors.

Another limitation of conventional test strip readers is that they are not sensitive enough to detect small variations in color on the test strips. Thus, commercial readers might return the same result for multiple samples of slightly varying concentration simply because they are not able to resolve the differences in color between the samples.

Further, it has been found that commercial test strip readers produce null results at low analyte concentrations and become saturated at high analyte concentrations. For instance, increasing the analyte concentration beyond a certain amount produces no corresponding change in the color intensity detected by the reader, even though there is a perceptible change in the color of the test strip. Thus, the detection range of commercial readers is quite limited or narrow-range.

SUMMARY OF THE INVENTION

The present invention provides improved techniques for colorimetric based test strip analysis and reader system. In one aspect of the invention, a method of test strip analysis is provided. The method includes: illuminating a test strip wetted with a sample with select spectrums of light, wherein the test strip includes test pads that are configured to change color in the presence of an analyte in the sample; obtaining at least one digital image of the test strip; and analyzing color intensity from the at least one digital image against calibration curves to determine an analyte concentration in the sample with correction for one or more interference substances in the sample that affect the color intensity.

The method can further include: obtaining at least one digital image of the calibration pads, wherein the calibration pads have color reference patches that make up a series scale of colors of known chromaticity; analyzing a color of the color reference patches from the at least one digital image of the calibration pads by i) splitting the at least one digital image of the calibration pads into its component red, green and blue (RGB) channels, and ii) measuring an intensity of each of the RGB channels; obtaining plots of the intensity of each of the RGB channels against the known chromaticity of the color reference patches; and storing the plots.

Further, the method can also include: creating the calibration curves by: obtaining at least one digital image of the calibration pads and of test strips wetted with a series of analyte solutions having known pH at various analyte concentrations; adjusting the color intensity from the at least one digital image of the test strips using a normalization factor determined from the plots; and plotting the color intensity from the at least one digital image of the test strip against the various analyte concentrations to form the calibration curves. The creating of the calibration curves can be repeated x times with additional series of analyte solutions having a different known pH at the various analyte concentrations to obtain the calibration curves for a range of pH values. The creating of the calibration curves can be repeated y times with the series of analyte solutions having interference substances added to obtain the calibration curves for the interference substances.

In another aspect of the invention, a calibration method is provided. The method includes: creating calibration curves by: obtaining at least one digital image of calibration pads and of test strips wetted with a series of analyte solutions having known pH at various analyte concentrations, wherein the calibration pads have color reference patches that make up a series scale of colors of known chromaticity; and plotting the color intensity from the at least one digital image of the test strips against the various analyte concentrations to form the calibration curves.

In yet another aspect of the invention, a reader device is provided. The device includes a processor, connected to a memory, the processor being configured to perform: illuminating a test strip wetted with a sample with select spectrums of light, wherein the test strip includes test pads that are configured to change color in the presence of an analyte in the sample; obtaining at least one digital image of the test strip; and analyzing color intensity from the at least one digital image against calibration curves to determine an analyte concentration in the sample with correction for one or more interference substances in the sample that affect the color intensity.

A more complete understanding of the present invention, as well as further features and advantages of the present invention, will be obtained by reference to the following detailed description and drawings.

BRIEF DESCRIPTION OF THE DRAWINGS

FIG. 2 is a diagram illustrating some exemplary interference parameters according to an embodiment of the present invention;

FIG. 3 is a diagram illustrating the effect pH has on the appearance of a nitrite test pad exposed to different nitrite concentrations according to an embodiment of the present invention;

FIG. 4 is a diagram illustrating the color intensity of the nitrite pad on a test strip after dipping in nitrite solutions with different concentrations and pHs according to an embodiment of the present invention;

DETAILED DESCRIPTION OF PREFERRED EMBODIMENTS

Provided herein are techniques for colorimetric based test strip analysis and reader system with improved accuracy and expanded detection range as compared to conventional, commercially-available test strip readers. As will be described in detail below, the present techniques conveniently employ readily available consumables such as commercially-available test strips and leverage the advanced imaging and communication capabilities of mobile technology (e.g., via smartphone or tablet) to extract color intensity data from the test strips. Further, the present techniques employ a calibration procedure that leverages machine-learning processes to build an application (or "App") with interference correction to compensate for the presence of substances in a sample that affect the measurement of other substances.

Figure 1:
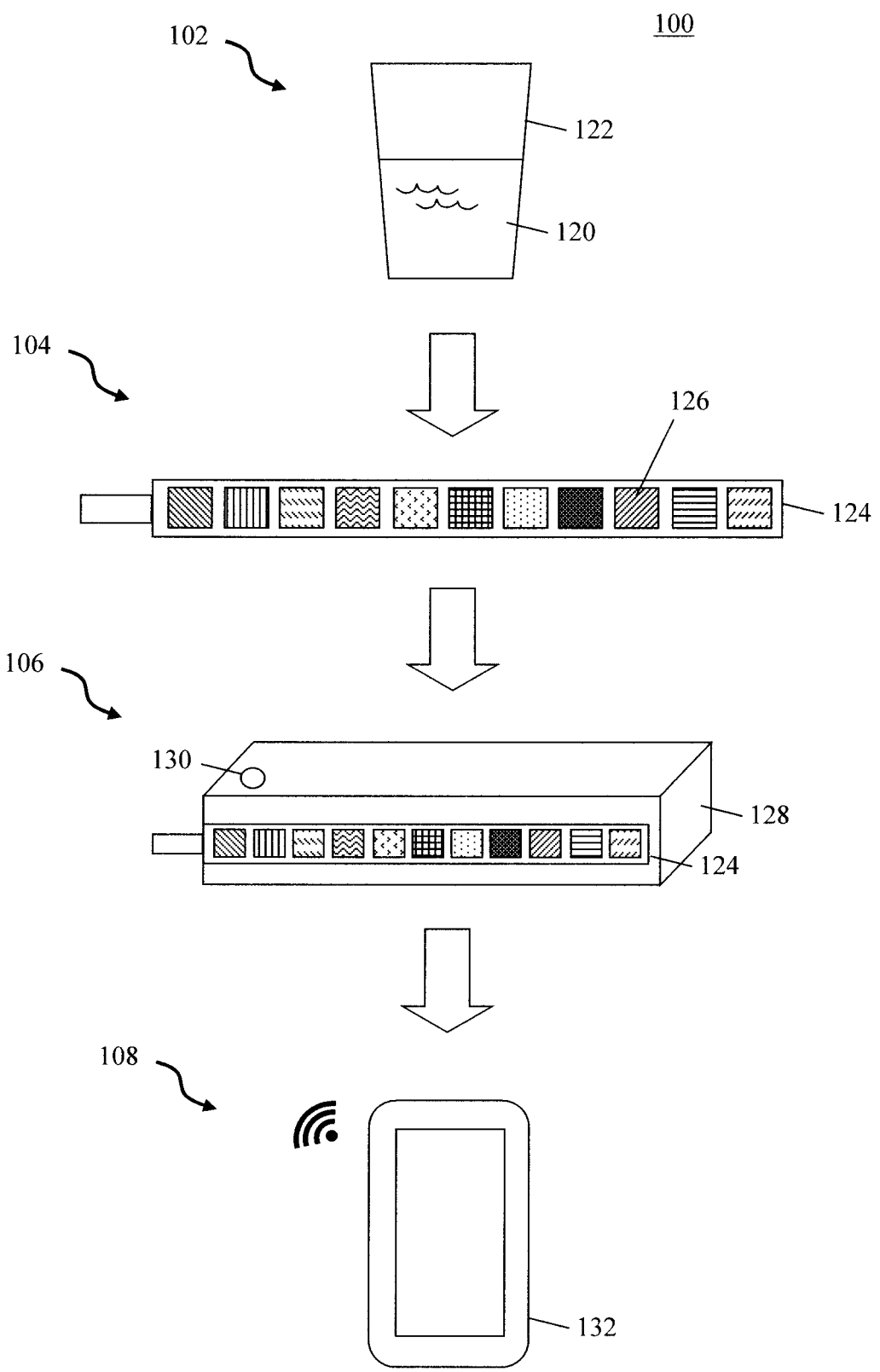
FIG. 1 is a diagram illustrating an exemplary methodology for test strip analysis using the present test strip analysis and reader system according to an embodiment of the present invention.

Methodology 100 in FIG. 1 provides an overview of the present test strip analysis and reader system. As shown in step 102, a sample 120 is provided. By way of example only, the sample 120 may be a sample collected from a patient for urinalysis in a collection cup 122.

In step 104, the sample 120 is contacted with a (commercially-available) test strip 124. For instance, the test strip can be simply dipped into the sample 120 present in collection cup 122. As shown in step 104, the test strip 124 contains at least two test pads 126 (i.e., at least one $2^{nd}$ test pad is needed to correct for interference in the $1^{st}$ test pad—see below). The test pads 126 are configured to change color in the presence of a particular analyte. The color intensity generally indicates the concentration of the analyte in the sample 120. For instance, commercially-available test strips for urinalysis may each include test pads 126 for glucose, protein, creatinine, pH, etc. Differences in the concentration of these analytes in the sample 120 cause the color intensity of the corresponding test pad 126 to change. For example, a higher concentration of creatinine might result in a darker color change on test pad 126, as compared to another test strip dipped into a sample with lower creatinine concentration.

In step 106, the test strip 124 is placed on the present sensing platform 128 and a digital image of the test strip 124 is taken. The digital image is taken using a camera which, according to an exemplary embodiment, is the camera present on a mobile device such as a smartphone, tablet and/or other electronic device. For instance, as shown in step 106, the sensing platform 128 can include a window 130 corresponding to the location of the camera on the mobile device. Thus, the mobile device is simply placed on the sensing platform with its camera facing the window 130, and an image is taken. Alternatively, a digital camera may instead be used to capture the digital image, which is then processed by the mobile device App.

In step 108, the digital image is processed. According to an exemplary embodiment, the digital image is both taken and analyzed using a mobile device 132. The mobile device 132 runs an App that performs the analytics on the image data. The App has built-in interference correction to account for the presence of substances that affect the measurement of other substances. Data collected and analyzed by the mobile device 132 is then transmitted wirelessly to a computer and/or cloud for further analysis and/or storage. By way of example only, the test strip images can be obtained and analyzed (via the present sensing platform 128) by a patient using his/her mobile device (e.g., smartphone, tablet and/or other electronic device) which is running the App. The mobile device transmits the image and analysis data to the cloud where it is stored and/or accessed by other computer systems, such as by a doctor or hospital that monitors the health condition of the patient and/or provides feedback to the patient.

As provided above, the presence of a substance or substances in the sample can affect the measurement of other substances. This is referred to herein as "interference," and the substances that cause the interference are referred to herein as "interference substances." Interference can undesirably lead false positive and false negative results. See, for example, Simerville et al. "Urinalysis: A Comprehensive Review," American Family Physician, Volume 71, Number 6 (March 2005) (hereinafter "Simerville"), the contents of which are incorporated by reference as if fully set forth herein. For instance, TABLE 2 of Simerville provides a variety of factors that lead to false positives and false negatives in a test strip-based analysis. Take for instance the presence of ketones in a sample which can generate a false positive reading for glucose, whereas uric acid or vitamin C can generate a false negative for glucose. Advantageously, the present App will be calibrated using known interference parameters and machine learning to account for such false positive and false negative readings.

By way of example only, FIG. 2 provides a table 200 of some exemplary interference parameters. For instance, as shown in table 200, the pH of a sample can affect the nitrite, protein and specific gravity measurements. The specific gravity of the sample in turn can affect nitrite, glucose, blood and leucocyte measurements, whereas the presence of nitrite in a sample can affect measurement of urobilinogen, and vice versa. The test pad color changes when these substances are introduced. The changes in color, if not corrected, will introduce error in the concentration reading.

Figures 5, 6:
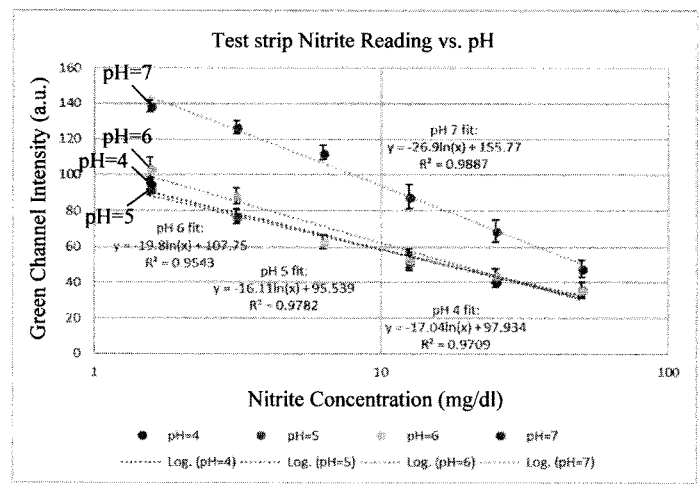
FIG. 5 is a diagram illustrating an example of a nitrite pad which showed 91% of color intensity according to an embodiment of the present invention.
FIG. 6 is a diagram illustrating the color intensity of the nitrite pad fitted as a function of pH according to an embodiment of the present invention.

See, for example FIG. 3, which illustrates the effect (interference parameter) pH has on the appearance of the nitrite test pad for different nitrite concentrations. This effect is clearly evident from the plot in FIG. 4 which illustrates the color intensity of the nitrite pad on a test strip after dipping in nitrite solutions with different concentrations and different pHs. The nitrite detection is more sensitive for lower pHs. The sensitivity, or color change, decreases at higher pH, especially at pH greater than 6. For pHs in the range of 4 to 5, the nitrite readings are very similar. At pH 6, the sensitivity starts to decrease. At pH 7, the nitrite detection sensitivity drops significantly. Table 500 in FIG. 5 is an example of a nitrite pad which showed 91% of color intensity. With the same color intensity, the nitrite concentration for a sample with pH=7 can be 15 times higher than a sample with pH=4.

Figure 7:
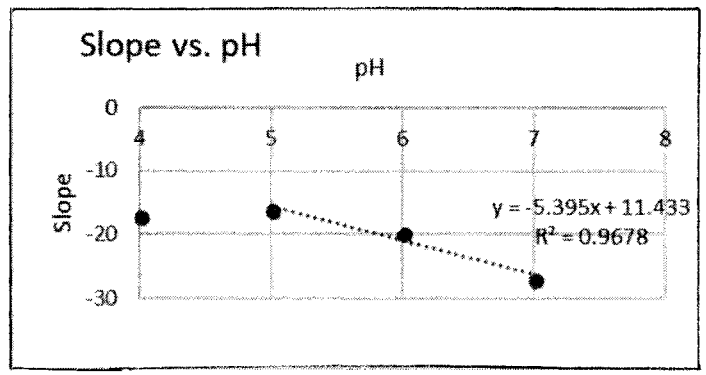
FIG. 7 is a diagram illustrating, from the data in FIG. 6, the slope of the logarithmic fit having been extracted for a given pH according to an embodiment of the present invention.
Figure 8:
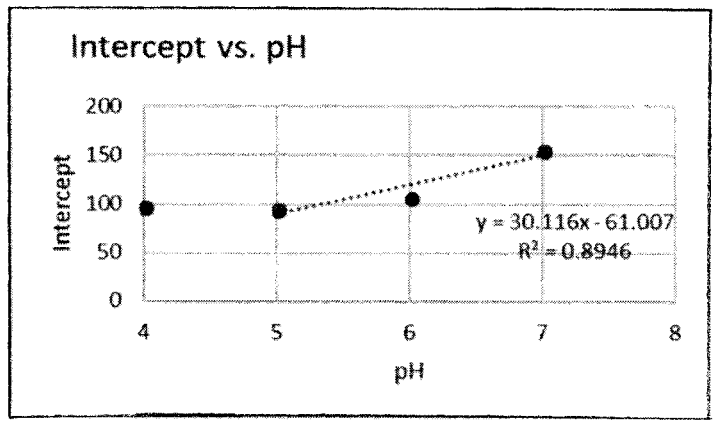
FIG. 8 is a diagram illustrating, from the data in FIG. 6, the intercept of the logarithmic fit having been extracted for a given pH according to an embodiment of the present invention.

Advantageously, the present App that performs the analytics on the image data is trained to correct for these color changes. For instance, fitting the color intensity of the nitrite pad as a function of pH enables one to empirically determine logarithmic fits at each pH value. See FIG. 6. From this data, the slope and intercept of the logarithmic fit can be extracted for a given pH. See FIG. 7 and FIG. 8, respectively. Thus, if the sensor values corresponding to nitrite and pH test pads are known, then the correct nitrite concentration can be calculated despite the interference caused by variations in the pH. Similarly, this technique can be extended to multiple interfering components where calibration measurements are performed with multiple interfering components, and multiple variable fits are used to extract the corrected concentrations of the target analyte.

Figure 9:
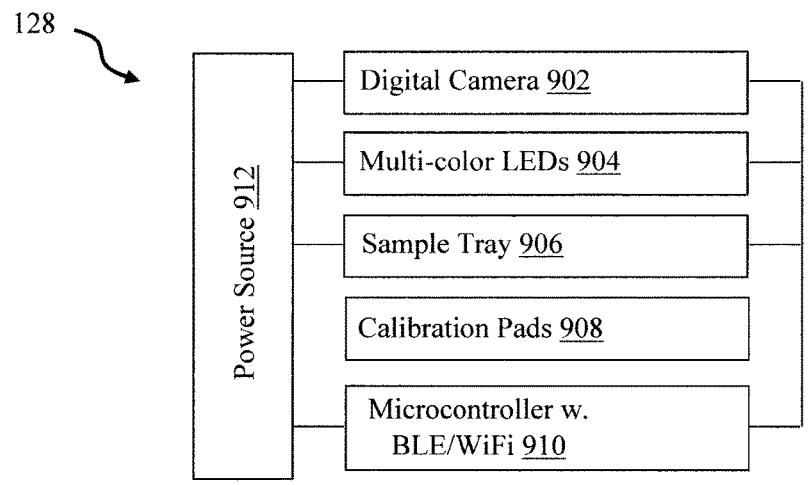
FIG. 9 is a schematic diagram illustrating the components in the present sensing platform according to an embodiment of the present invention.

A schematic diagram of the components in sensing platform 128 is shown in FIG. 9. As shown in FIG. 9, sensing platform 128 includes a digital camera 902, multi-color light emitting diodes (LEDs) 904 (and/or other light sources including ambient), sample tray 906, calibration pads 908, a microcontroller 910, and a power source 912 (e.g., a battery or other suitable power source). By "multi-color LEDs" it is meant that multiple LEDs are present which emit light at different colors. Each of these LEDs can be individually turned on to provide different color illumination, thus providing illumination with select spectrums of light. As highlighted above, the digital camera 902 can be a component of a mobile device (such as a smart phone, tablet and/or other electronic device) that is placed on the sensing platform 128 to capture and analyze test strip image data. In general, however, any digital camera configured to capture digital images of a test strip loaded in the sensing platform 128 can be employed.

Use of multi-color LEDs 904 as a light source provides the capability of selecting particular wavelengths of light to illuminate the test strip pads for measurement. However, as highlighted above, other illumination systems are also contemplated herein. For instance, if one or more surfaces of the sensing platform are transparent, then a sample can be illuminated from the opposite side of the sample away from the digital camera. Further, mobile devices like smartphones and tablets with imaging capabilities also typically include a light source (i.e., a flash) which can also be employed as the illumination system in sensing platform 128.

Sample tray 906 is used to load a sample test strip into the sensing platform 128. Namely, the sample tray 906 is extracted from the sensing platform either manually by a user and/or in an automated manner via microcontroller 910. At least one sample test strip is placed in the sample tray 906, and the sample tray 906 with loaded test strip is retracted back into the sensing platform 128 for imaging/analysis. When loaded in the sensing platform 128, sample tray 906 places the test strip properly in the field of view of the digital camera 902.

Calibration pads 908 provide color reference patches for the sample test strip pads during measurement, and thus are preferably located adjacent to the sample test strip, at a same focal plane as the test strip and within the field of view of the digital camera 902. For instance, according to an exemplary embodiment, the calibration pads 908 consist of a series scale of chromaticity of black/red/green/blue/white (grey). Preferably, the calibration pads are made of the same or similar material as the test strip, but with permanent color ink, to minimize any differences in surface reflection that might affect the measurements. According to an exemplary embodiment, the calibration pads 908 can be affixed to, or printed on, the inner surface of the sensing platform adjacent to the loaded sample tray 906.

In order to prevent degradation of the calibration pads 908 over time due to exposure to dust or other damage which can affect measurements, embodiments are contemplated herein where a sliding cover is placed over the calibration pads 908 when the sensing platform is not in use. When a test strip is loaded into the sample tray 906, the cover is retracted or removed exposing the calibration pads 908 during controlled illumination (i.e., illumination with select spectrums of light) and imaging. Operation of the cover can be manual or automated (e.g., via microcontroller 910). For instance, the cover can be accessible to the user who removes and replaces it before and after use of the sensing platform. Alternatively, the microcontroller 910 can be configured to retract the cover whenever test strip loading (via the sample tray 906) is detected.

Figure 10:
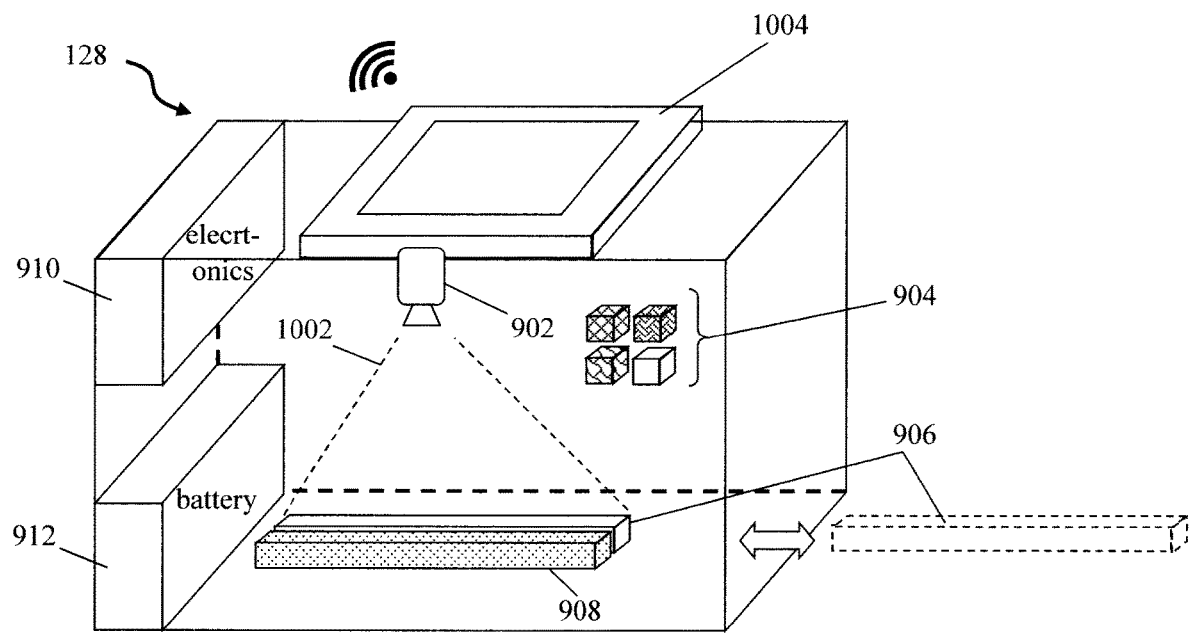
FIG. 10 is a diagram illustrating an exemplary configuration of the sensing platform configured to acquire/analyze test strip image data in reflection mode according to an embodiment of the present invention.

One exemplary configuration of the sensing platform 128 configured to acquire/analyze test strip image data in reflection mode is shown illustrated in FIG. 10. As shown in FIG. 10, the sample tray 906 and calibration pads 908 are located below the digital camera 902 and illumination system (in this case multi-color LEDs 904). In no particular order, the multi-color LEDs may include red, green, blue and white LEDs. Ultra violet (UV) or infrared (IR) illuminations may be used as well. During imaging, controlled light illumination (i.e., illumination with select spectrums of light) from the multi-color LEDs 904 incident on the sample tray 906 and calibration pads 908 is reflected back towards the digital camera 902 above, which captures a digital image(s). Multiple images can be collected, for example using different illumination colors (i.e., for different test pads), to maximize the sensitivity to the color changes of the different test pads. Both the sample tray 906 and calibration pads 908 are in the field of view 1002 of the digital camera 902.

The term "digital image," as used herein, generally refers to color still and/or color digital video images captured by the digital camera. For instance, as will be described in detail below, still digital images of the test strip/calibration pads can capture color intensity data. However, in the case of some analytes such as creatinine, the detection chemistry is time sensitive. Namely, the test pad color changes over time. Thus, for instance, the color of the pads one minute after dipping the test strip into a sample containing creatinine can be different when viewed 20 minutes later. In order to analyze the rate of color intensity change in such time sensitive samples, it may be desirable to capture digital video images or a series of still digital images over a monitored and recorded period of time. The rate of the change in color intensity can be used as a sensing parameter to determine the concentration of analyte.

As illustrated in FIG. 10, the sample tray 906 can be inserted/retracted from the sensing platform 128 whereby, when retracted, a test strip is placed on the sample tray 906 (or removed from the sample tray 906 and discarded after use). The sample tray 906 is then reinserted into the sensing platform, which places the test strip adjacent to the calibration pads 908. As provided above, operation of the sample tray 906 can be performed manually, or in an automated manner via the microcontroller 910. Microcontroller 910 also contains Bluetooth low energy (BLE) and/or WiFi electronics configured to transmit image data (i.e., to a mobile device, cloud and/or other computer system for storage/analysis—see above).

In the present example, digital camera 902 is a component of a mobile device 1004 (e.g., a smartphone or tablet). As provided above, the mobile device 1004 is configured to acquire and analyze the image data and/or transmit the data to the cloud and/or other computer system for storage/analysis. Power source 912 (e.g., a battery) powers the various components of sensing platform 128.

Figure 11:
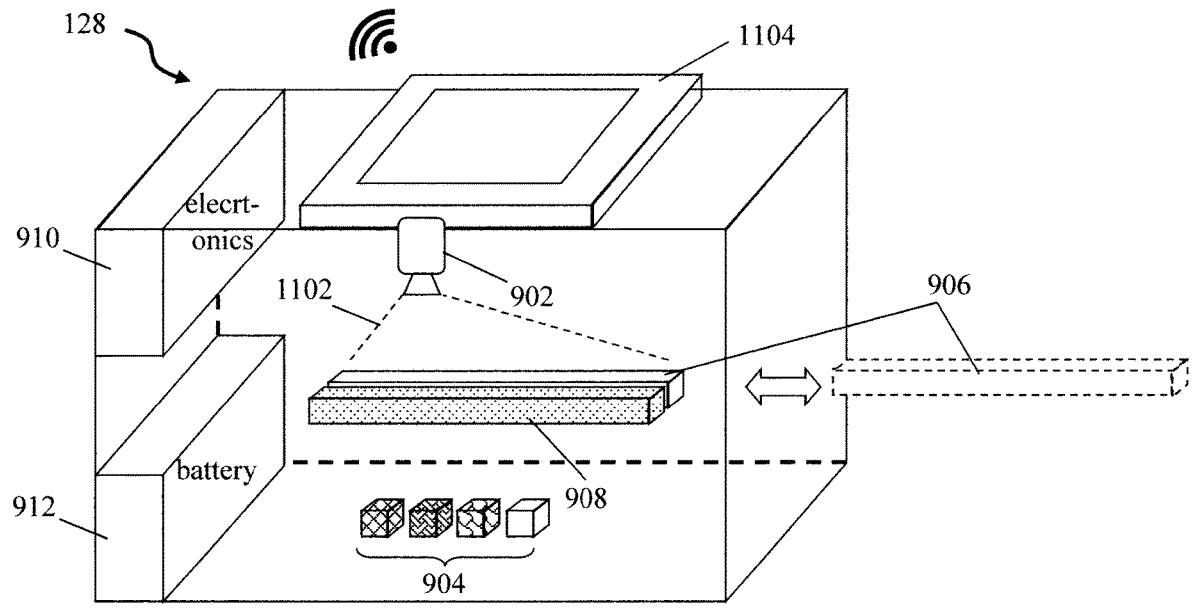
FIG. 11 is a diagram illustrating an exemplary configuration of the sensing platform configured to acquire/analyze test strip image data in transmission mode according to an embodiment of the present invention.

An exemplary configuration of the sensing platform 128 configured to acquire/analyze test strip image data in transmission mode is shown illustrated in FIG. 11. This transmission mode configuration is similar to the sensing platform design presented in FIG. 10, except that the illumination system (e.g., multi-color LEDs 904 are instead located below the (in this case transparent) sample tray 906 with also transparent test strip and transparent calibration pads 908. Namely, as shown in FIG. 11, the sample tray 906 and calibration pads 908 are located between the digital camera 902 above and the illumination system (in this case multi-color LEDs 904) below. In no particular order, the multi-color LEDs may include red, green, blue and white LEDs. During imaging, light from the multi-color LEDs 904 passes through the sample tray 906 and calibration pads 908 (both of which must be transparent) towards the digital camera 902 which captures an image(s). Multiple images can be collected, for example using different illumination colors (i.e., for different test pads), to maximize the sensitivity to the color changes of the different test pads. Both the sample tray 906 and calibration pads 908 are in the field of view 1102 of the digital camera 902.

In the same manner as above, the sample tray 906 can be inserted/retracted from the sensing platform 128 whereby, when retracted, a test strip is placed on the sample tray 906 (or removed from the sample tray 906 and discarded after use). The sample tray 906 is then reinserted into the sensing platform, which places the test strip adjacent to the calibration pads 908. As provided above, operation of the sample tray 906 can be performed manually, or in an automated manner via the microcontroller 910. Microcontroller 910 also contains Bluetooth low energy (BLE) and/or WiFi electronics configured to transmit image data (i.e., to a mobile device, cloud and/or other computer system for storage/analysis—see above).

In the present example, digital camera 902 is a component of a mobile device 1104 (e.g., a smartphone or tablet). As provided above, the mobile device 1104 is configured to acquire and analyze the image data and/or transmit the data to the cloud and/or other computer system for storage/analysis. Power source 912 (e.g., a battery) powers the various components of sensing platform 128.

Figure 12:
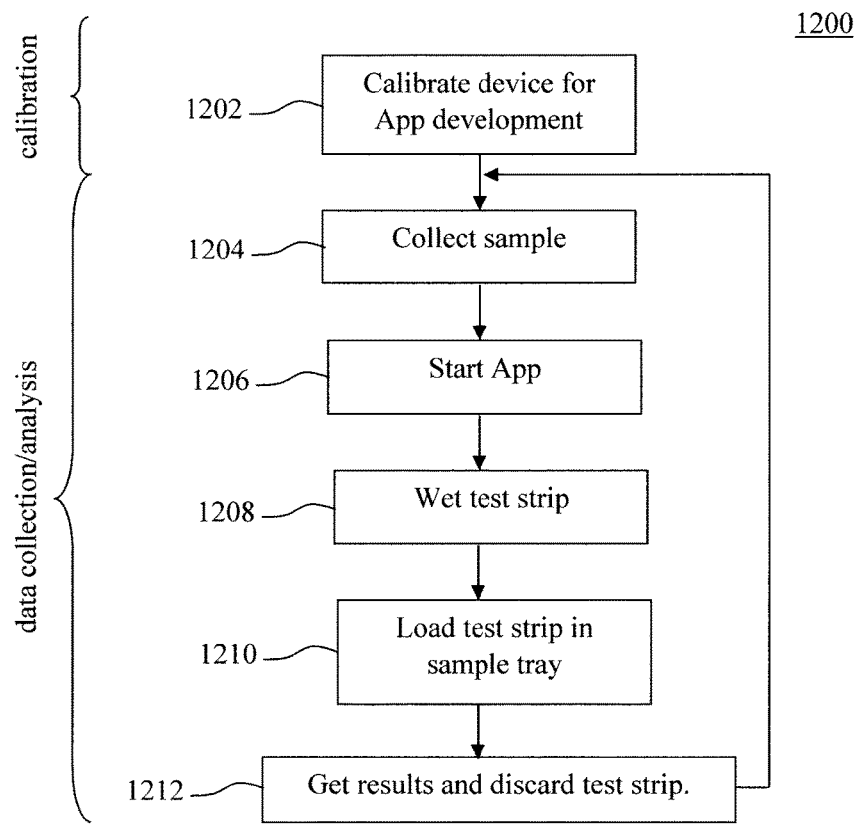
FIG. 12 is a diagram illustrating an exemplary methodology for operation of the present sensing platform according to an embodiment of the present invention.

The overall general operation of the present sensing platform 128 is now described by way of reference to methodology 1200 of FIG. 12. In step 1202 (an initial calibration step), the App that will perform the analytics on the image data is calibrated for interference correction. As provided above, this calibration will account for the presence of substances that affect the measurement of other substances. An exemplary calibration procedure will be described in detail below. In general, the procedure involves measuring analyte solutions of known concentration at a range of different pHs. The solutions are then spiked with an interference substance and/or a combination of interference substances. The measurement process is then repeated. The results obtained at each iteration are used to train the App to learn the color intensity values for the analyte at a range of pHs and in the presence of one or more interference substances.

Once the App has been calibrated, data collection and analysis can then be performed. For instance, in step 1204 a sample is collected. By way of example only, the sample can be a clinical analyte collected from a patient (e.g., for urinalysis). In step 1206, the mobile device is placed on the sensing platform and the (now-calibrated) App is started on the mobile device. As provided above, the mobile device can be a smartphone, tablet and/or other electronic device. According to an exemplary embodiment, the mobile device belongs to the patient/user for which the analysis is being performed. Via their mobile devices, users can provide patient profile information (e.g., height, weight, etc.) as well as information about the test being performed (e.g., orientation and configuration of the test strip being used, urinalysis, blood glucose monitoring, etc.).

The test strip is wetted with the sample (see step 1208) and then placed on the sample tray and loaded into the sensing platform (see step 1210). In step 1212, results are obtained from analysis of the image data obtained from the test strip, after which the test strip is removed from the sensing platform and discarded. The sample tray is preferably removable so that it can be cleaned and disinfected after each use. Since the calibration is test strip specific (i.e., specific to the type/configuration/brand of test strip), means for identifying the type/configuration/brand, etc. of test strip are contemplated herein. For instance, image recognition of the brand mark on the test strip, if there is one, can be employed. Alternatively, the user can provide this information to the App (e.g., via their mobile device). Also, the mobile device can be used to scan the bar code and/or other machine-readable code on the test strip packaging. For proper readings to be made, the test strip(s) need to be properly inserted into the sensing platform. Thus, according to an exemplary embodiment, the position and orientation of the test strip placement is controlled by the sample tray. For instance, improperly positioned test strips will result in an error message and/or sample tray will not be insertable into the sensing platform if the test strip(s) is improperly placed on the sample tray.

According to an exemplary embodiment, the App run on the mobile device controls the sensing platform including the illumination system whereby, in step 1212, the App automatically selects the illumination source. For instance, when the illumination source includes multi-color LEDs (see above), the App can select which color LED(s) to turn on during imaging (i.e., for select spectrums of light) and may collect multiple images with different illumination conditions to maximize the sensitivity of the different test pads. The color of the test pad is due to absorption of light at different wavelengths. For example, a blue color test pad is due to the absorption of light in the red spectrum, a magenta color test pad is due to absorption of light in the green spectrum, and a reddish color test pad is due to absorption of light in the blue spectrum. Thus, illuminating the test pad with the color of the light that has maximum absorption can increase the detection sensitivity. When the illumination source is a light source on the mobile device (e.g., built-in flash), then the App will preferably control when that light source is turned on/off, and the intensity of the illumination.

The App run on the mobile device also controls the digital camera to take one or more still or video digital images of the test strip and calibration pads in step 1212. As provided above, the digital camera might itself be part of the mobile device. Thus, the mobile device is placed on the sensing platform in a manner that places the test strip and calibration pads in line of sight of the mobile device's camera (see, e.g., FIGS. 10 and 11—described above). Each of the still digital images are timestamped. In the case of digital video images, starting the App can also start a timer that runs concurrently with the video. That way, data extracted from the images can be analyzed at specific time points. As described above, providing a temporal reference to the present analytics is needed where the detection chemistry is time sensitive (e.g., in the case of creatinine). In addition, the color intensity change as a function of time, i.e., rate of change, is typically related to the concentration of the analyte. As such, the rate of change can be used to determine the concentration of the analyte, especially for long reaction time and time-sensitive detection chemistries.

Further, the App will determine a normalization factor for the illumination and digital camera set up by analyzing the images of the calibration pads 908 in step 1212. This normalization procedure will be described, for example, in conjunction with the description of methodology 1300 of FIG. 13, below. In general however, the process involves obtaining digital images of the calibration pads 908, and then analyzing the color intensity of the digital images against the known chromaticity of the calibration pads 908 to be used as a normalization factor when sample measurements are taken. Basically, sample image data obtained using the same digital camera and illumination source will be normalized based on color reference patches (i.e., the calibration pads 908) of known chromaticity.

In step 1212, the App will also compare the sample pad analyte color intensity values with calibrated curve(s) to determine analyte concentration with interference correction and give readout value. This process for interference correction will be described, for example, in conjunction with the description of methodology 1400 of FIG. 14, below. As provided above, this process generally involves measuring analyte solutions of known concentration at a range of different pHs, and then spiking the solutions with interference substances individually or in combination and repeating the measurement process. The results obtained at each iteration are used, via machine learning and/or multivariable fits, to automatically create calibration curves for each of the interference substances and combinations of interference substances at the various different pH values. Finally, the App will store the (timestamped) test results and, if appropriate, send the results, e.g., to the cloud, the user/patient and/or care taker/health care provider/institution such as a hospital, doctor or nurse, etc.

Figure 13:
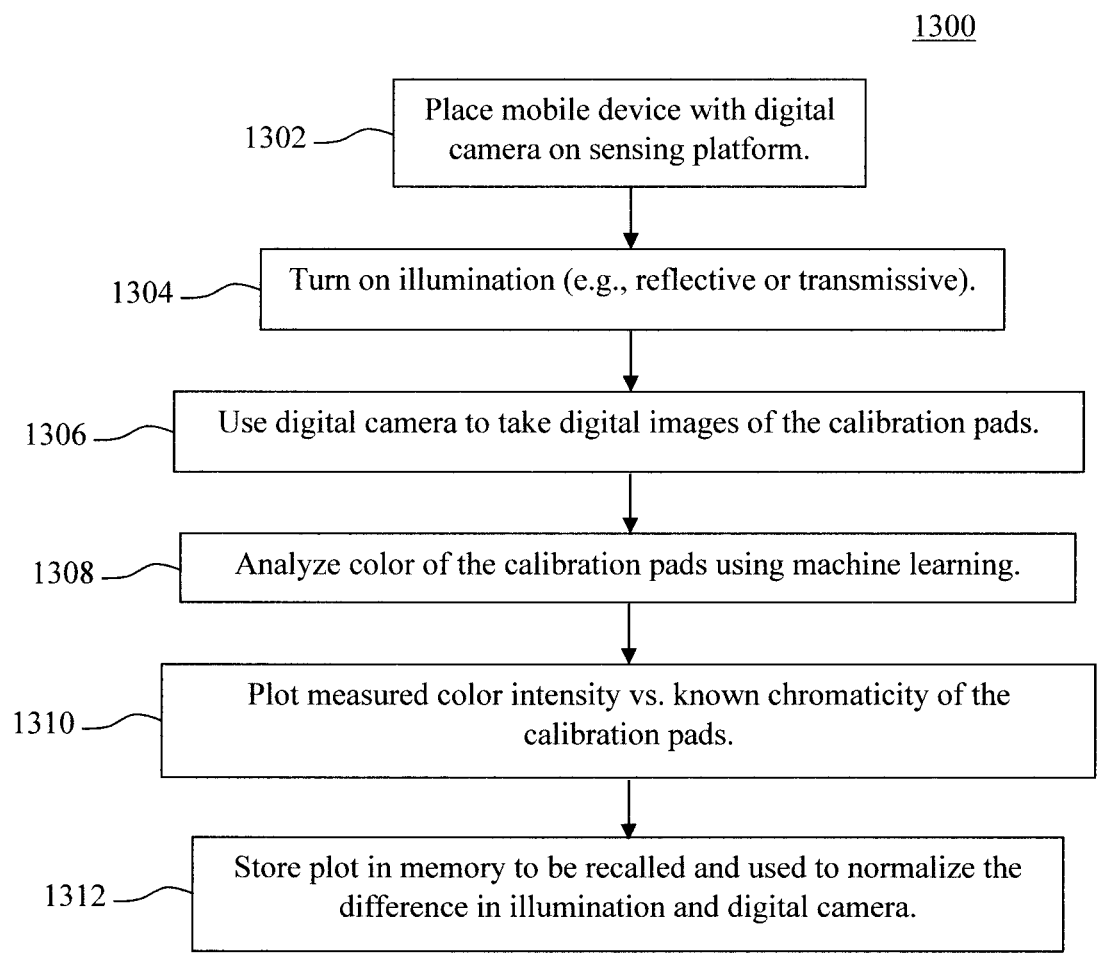
FIG. 13 is a diagram illustrating an exemplary methodology for determining a normalization factor for the illumination and digital camera set up via calibration pads according to an embodiment of the present invention.

FIG. 13 provides an exemplary methodology 1300 for determining a normalization factor for the illumination and digital camera set up via the calibration pads 908. Methodology 1300 can be performed using any of the sensing platform configurations described herein including, but not limited to, the sensing platform shown in FIG. 10 (reflection mode) and/or the sensing platform shown in FIG. 11 (transmission mode)—both described above.

In step 1302, the mobile device with digital camera 902 is placed on the sensing platform 128. See, for example, mobile device (e.g., smartphone or tablet) 1004 (FIG. 10) and/or 1104 (FIG. 11). In step 1304, the illumination is turned on. See, for example, multi-color LEDs 904 which can be oriented for measurement in reflection mode (FIG. 10) or transmission mode (FIG. 11). Alternatively, as provided above, illumination can be provided by a light (e.g., flash) component of the mobile device and/or via ambient light incident on the sensing platform.

In step 1306, the digital camera 902 is used to take digital images of the calibration pads 908. When multi-color LEDs are used, multiple images are preferably collected where the calibration pads are illuminated sequentially with the different individual LED colors. According to an exemplary embodiment, the calibration pads 908 include color reference patches that make up a series scale of red, green and blue colors of known chromaticity, as well as black and white grey scale references.

In step 1308, the color of the pads is analyzed from the digital images (obtained in step 1306). According to an exemplary embodiment, this analysis involves first using image recognition and machine learning to identify, select and crop pads of interest from the images. The goal is to correlate the intensity of a given color reference patch in the image with the known chromaticity of that same patch. Thus, each color reference pad of interest can be selected and cropped in the image for individual analysis. Image recognition in the App can involve simple pattern recognition, which recognizes and differentiates the test pads and reference patches. For instance, if the test strip and camera location or magnifications are all fixed, patches can simply be identified by the location information on the image. However, if the location registration is not precise, then image recognition and machine-leaning techniques are likely needed. The next task is to perform a color analysis on each of the pads of interest. Here the digital image of each pad is split into its component red, green and blue (RGB) channels, and the intensity of each RGB channel is measured.

In step 1310, the measured color intensity of each RGB channel is plotted against known chromaticity of the color reference patches. The known chromaticity includes values for each RGB channel to enable normalization or scaling so that a qualitative concentration of the analyte can be obtained. In step 1312, the plots obtained are stored in memory by the APP. This enables the plots to be recalled and used to normalize the differences in illumination and digital camera characteristics. Namely, there will likely be differences in the measured color intensity of the patches versus their known chromaticity. This discrepancy can be attributed to a variety of factors including the illumination source and the digital camera used to obtain the images. However, these factors can be corrected for by normalizing later readings using the stored plots.

Figure 14:
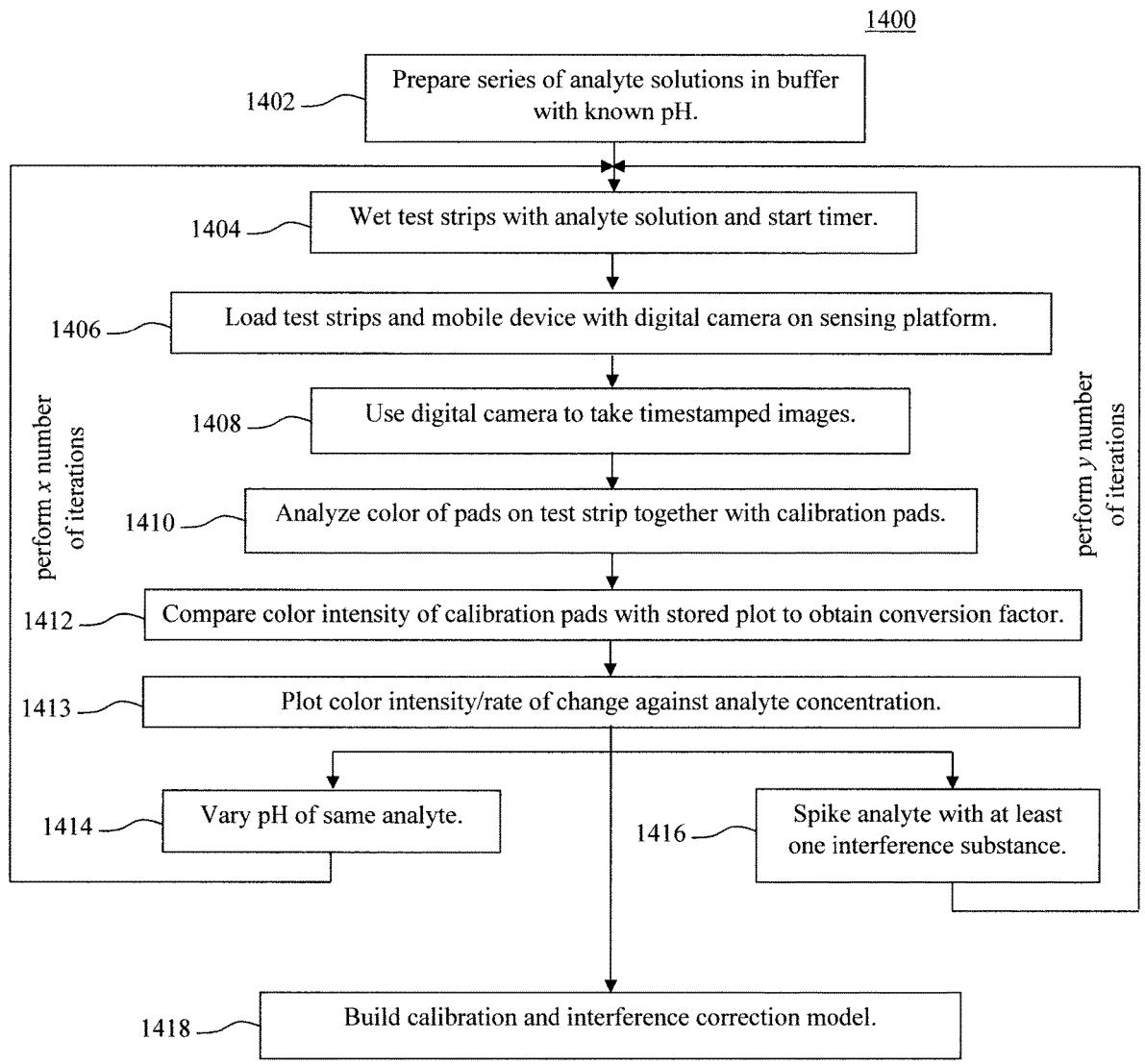
FIG. 14 is a diagram illustrating an exemplary methodology for interference correction according to an embodiment of the present invention.

FIG. 14 is a diagram illustrating an exemplary methodology 1400 for interference correction. Methodology 1400 can be performed using any of the sensing platform configurations described herein including, but not limited to, the sensing platform shown in FIG. 10 (reflection mode) and/or the sensing platform shown in FIG. 11 (transmission mode)—both described above.

In step 1402, a series of analyte solutions are prepared in a buffer with known pH. Thus, all of the analyte solutions have the same pH. However, the concentration of the analyte(s) is varied amongst the solutions (see, for example, FIG. 3—described above). Each solution contains at least one analyte (corresponding to the test pads on the test strip(s) being used) at a given concentration. Optionally, multiple analytes may be present in each solution. For illustrative purposes only, some exemplary analytes include, but are not limited to, nitrite, protein, glucose, blood, leucocytes and/or urobilinogen. As provided above, pH is one interference factor that affects color intensity. Thus, later steps involve varying the pH and repeating the measurement process. At this stage, however, the pH is constant.

In step 1404, test strips 124 are then wetted with the analyte solutions, and the timer is started. One test strip 124 is used for each solution. However, each solution might contain more than one analyte. As such, each test strip 124 might also detect more than one analyte. A timer is used for those analytes where the detection chemistry is time sensitive. Starting the clock when the solutions are contacted with the test strips 124 provides a timeframe reference for the analysis. Thus, the digital (still or video) images subsequently taken of the test strips 124 can be accurately timestamped via the timer.

In step 1406, the test strips 124 are inserted into the sensing platform 128 (e.g., via the sample tray 906) and the mobile device with digital camera 902 is placed on the sensing platform 128. See, for example, mobile device (e.g., smartphone or tablet) 1004 (FIG. 10) and/or 1104 (FIG. 11). In step 1408, the digital camera 902 is used to take (timestamped) digital (still or video) images of the test strips 124 and calibration pads 908. As provided above, the calibration pads 908 include color reference patches that make up a series scale of black, white, red, green and blue colors of known chromaticity.

In step 1410, the color of the pads 126 of the test strips 124 are analyzed together with the color from the color reference patches. According to an exemplary embodiment, this analysis involves first using image recognition and machine learning to identify, select and crop pads of interest (i.e., pads 126 of the test strips 124 and the color reference patches from calibration pads 908) from the images. A color analysis is then performed on each of the pads of interest by splitting the digital image of each pad into its component RGB channels and measuring the intensity of each RGB channel.

In step 1412, the measured color intensity of the color reference patches is compared with the stored color reference plot (see step 1312 of methodology 1300 described in conjunction with the description of FIG. 13, above). The measured color intensity may also be used to calculate chromaticity, such as hue, saturation and intensity. As described above, the stored color reference plot is used to determine a normalization factor that accounts for differences in the illumination and/or digital camera characteristics (i.e., when compared to known chromaticity of the color reference patches). The normalization factor is then used to adjust the test strip measurements to account for these differences. To use a simple example, for identical illumination and camera, the conversion factor should be 1. For instance, the light intensity can be calibrated against a group of grey scale patches, from white (100%), to gray (18%, 12%, etc.) and black. The same can be done for color reference patches. The color intensity of white can be scaled as 1, and gray as its corresponding values.

In step 1413, the color intensity and rate of change of intensity is plotted against analyte concentration. Later, the collective results (e.g., of multiple iterations with different interference substances and/or combinations of interference substances) will be used to build a calibration and interference correction model. Thus, in step 1413 the most sensitive RGB channel (in each iteration) is selected for use in building the model. By 'most sensitive' it is meant the spectrum range that has the largest change in absorption in the test pad and correlates best with the change in analyte concentration over the range of interest. As an alternative, instead of the most sensitive individual RGB channel, a weighted sum of two or more channels may be used if it provides greater sensitivity.

In step 1414, a series of solutions are prepared with the same analyte(s) at the same concentrations, but with a different (known) pH from the previous iteration. For instance, by way of example only, in one iteration all of the solutions have a pH=4. In the next iterations, all of the solutions have a pH=5, and so on. Steps 1402-1414 are then repeated x times (i.e., x>1) to obtain calibration curves (i.e., at least one calibration curve per iteration) for a range of pHs.

The same general process is performed for obtaining calibration curves for other interference substances added to the solutions both individually or in combination. Namely, in step 1416 the analyte solutions are each spiked with at least one interference substance. As shown in FIG. 14, steps 1402-1416 are then repeated y times (i.e., y>1) to obtain calibration curves (i.e., at least one calibration curve per iteration) for a range of different interference substances.

Preferably, the interference substances are evaluated at each of the pHs tested. For example, an iteration x can be performed at a first pH. The solution is then spiked with an interference substance(s) and an iteration y is performed at the first pH. Another iteration x is then performed at a second pH followed by another iteration y with a different interference substance or combination of interference substances at the second pH, and so on. At each iteration y a single interference substance or a combination of interference substances may be introduced into the analyte solutions. To use the illustrative non-limiting example provided in FIG. 2 above, one iteration y can employ nitrite as the interference substance, while another employs a combination of nitrite and urobilinogen.

In step 1418, the calibration curves from each iteration are used to build a calibration and interference correction model. According to an exemplary embodiment, multivariable regression analysis is performed on the measured results to fit equations relating the analyte concentration, pH, interference substance concentration(s), and other factors to the measured color intensities on multiple test pads. When measurements of sample analytes are taken (see, for example, step 1212 described in conjunction with the description of FIG. 12 above), this calibration and interference correction model is used to determine analyte concentration with interference correction and give an accurate readout value.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 15:
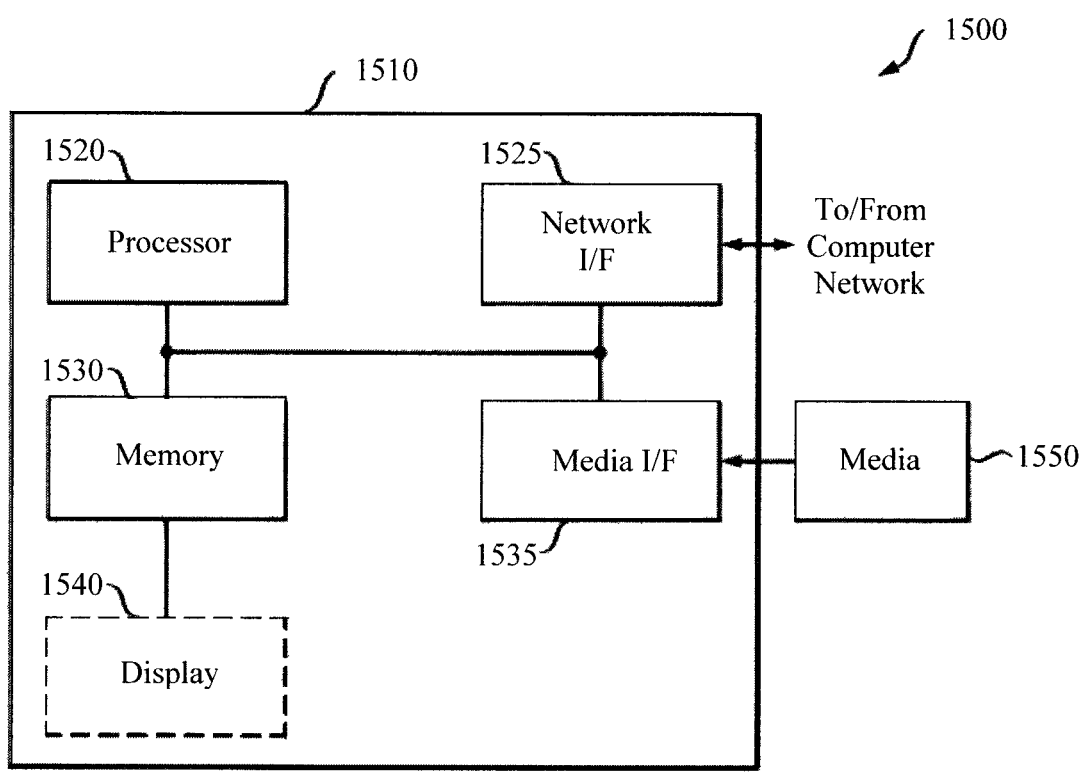
FIG. 15 is a diagram illustrating an exemplary apparatus for performing one or more of the methodologies presented herein according to an embodiment of the present invention.

Turning now to FIG. 15, a block diagram is shown of an apparatus 1500 that can be configured to perform one or more of the methodologies presented herein. For example, apparatus 1500 generally represents any of the mobile devices described herein and can be configured to perform one or more of the steps of methodology 100 (of FIG. 1), methodology 1200 (of FIG. 12), methodology 1300 (of FIG. 13) and/or methodology 1400 (of FIG. 14) described above. Apparatus 1500 includes a computer system 1510 and removable media 1550. Computer system 1510 includes a processor device 1520, a network interface 1525, a memory 1530, a media interface 1535 and an optional display 1540. Network interface 1525 allows computer system 1510 to connect to a network, while media interface 1535 allows computer system 1510 to interact with media, such as a hard drive or removable media 1550.

Processor device 1520 can be configured to implement the methods, steps, and functions disclosed herein. The memory 1530 could be distributed or local and the processor device 1520 could be distributed or singular. The memory 1530 could be implemented as an electrical, magnetic or optical memory, or any combination of these or other types of storage devices. Moreover, the term "memory" should be construed broadly enough to encompass any information able to be read from, or written to, an address in the addressable space accessed by processor device 1520. With this definition, information on a network, accessible through network interface 1525, is still within memory 1530 because the processor device 1520 can retrieve the information from the network. It should be noted that each distributed processor that makes up processor device 1520 generally contains its own addressable memory space. It should also be noted that some or all of computer system 1510 can be incorporated into an application-specific or general-use integrated circuit.

Optional display 1540 is any type of display suitable for interacting with a human user of apparatus 1500. Generally, display 1540 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method, comprising:
    illuminating a test strip wetted with a sample with select spectrums of light, wherein the test strip comprises test pads that are configured to change color in the presence of an analyte in the sample;
    obtaining at least one digital image of the test strip;
    analyzing color intensity from the at least one digital image against calibration curves to determine an analyte concentration in the sample with correction for one or more interference substances in the sample that affect the color intensity, wherein the method further comprises:
    obtaining at least one digital image of calibration pads, wherein the calibration pads have color reference patches that make up a series scale of colors of known chromaticity;
    analyzing a color of the color reference patches from the at least one digital image of the calibration pads by i) splitting the at least one digital image of the calibration pads into its component red, green and blue (RGB) channels, and ii) measuring an intensity of each of the RGB channels;
    obtaining plots of the intensity of each of the RGB channels against the known chromaticity of the color reference patches; and
    storing the plots.

2. The method of claim 1, wherein the illuminating further comprises:
    varying a color of illumination for different ones of the test pads.

3. The method of claim 1, wherein the at least one digital image comprises still or video digital images.

4. The method of claim 1, wherein the at least one digital image is timestamped, the method further comprising:
    timing when the test strip is wetted with the sample.

5. The method of claim 1, wherein the at least one digital image is obtained using a digital camera that is a component of a mobile device.

6. The method of claim 5, wherein the mobile device is a smartphone or tablet.

7. The method of claim 1, further comprising:
    creating the calibration curves by:
        obtaining at least one digital image of the calibration pads and of test strips wetted with a series of analyte solutions having known pH at various analyte concentrations;
        adjusting the color intensity from the at least one digital image of the test strips using a normalization factor determined from the plots; and
        plotting the color intensity from the at least one digital image of the test strips against the various analyte concentrations to form the calibration curves.

8. The method of claim 7, further comprising:
    repeating the creating of the calibration curves x times with additional series of analyte solutions having a different known pH at the various analyte concentrations to obtain the calibration curves for a range of pH values.

9. The method of claim 7, further comprising:
    repeating the creating of the calibration curves y times with the series of analyte solutions having interference substances added to obtain the calibration curves for the interference substances.

10. The method of claim 9, wherein the interference substances are added individually to the series of analyte solutions.

11. The method of claim 9, wherein a combination of two or more of the interference substances are added to the series of analyte solutions.

12. The method of claim 1, wherein the illuminating comprises:
    providing different color illumination using multiple light-emitting diodes (LEDs) which emit light at different colors.

13. A method, comprising:
    creating calibration curves by:
        obtaining at least one digital image of calibration pads and of test strips wetted with a series of analyte solutions having known pH at various analyte concentrations, wherein the series of analyte solutions all have a same pH, and analyte concentration is varied amongst the series of analyte solutions, and wherein the calibration pads have color reference patches that make up a series scale of black, white, red, green and blue colors of known chromaticity; and
        plotting the color intensity from the at least one digital image of the test strips against the various analyte concentrations to form the calibration curves.

14. The method of claim 13, further comprising:
    repeating the creating of the calibration curves x times with additional series of analyte solutions having a different known pH at the various analyte concentrations to obtain the calibration curves for a range of pH values.

15. The method of claim 14, further comprising:
    repeating the creating of the calibration curves y times with the series of analyte solutions having interference substances added to obtain the calibration curves for the interference substances.

16. The method of claim 13, further comprising:
illuminating a test strip wetted with a sample with select spectrums of light, wherein the test strip comprises test pads that are configured to change color in the presence of an analyte in the sample;
obtaining at least one digital image of the test strip; and
analyzing color intensity from the at least one digital image against the calibration curves to determine an analyte concentration in the sample with correction for one or more interference substances in the sample that affect the color intensity.

17. The method of claim 16, wherein the illuminating further comprises:
varying a color of illumination for different ones of the test pads.

18. A device, comprising:
a processor, connected to a memory, the processor being configured to perform:
illuminating a test strip wetted with a sample with select spectrums of light, wherein the test strip comprises test pads that are configured to change color in the presence of an analyte in the sample;
obtaining at least one digital image of the test strip;
analyzing color intensity from the at least one digital image against calibration curves to determine an analyte concentration in the sample with correction for one or more interference substances in the sample that affect the color intensity, wherein the processor is further configured to perform:
obtaining at least one digital image of calibration pads, wherein the calibration pads have color reference patches that make up a series scale of colors of known chromaticity;
analyzing a color of the color reference patches from the at least one digital image of the calibration pads by i) splitting the at least one digital image of the calibration pads into its component red, green and blue (RGB) channels, and ii) measuring an intensity of each of the RGB channels;
obtaining plots of the intensity of each of the RGB channels against the known chromaticity of the color reference patches; and
storing the plots.

19. The device of claim 18, wherein the at least one digital image is obtained using a digital camera that is a component of a mobile device.

20. The device of claim 19, wherein the mobile device is a smartphone or tablet.

21. The device of claim 18, wherein the processor when performing the illuminating is further configured to perform:
providing different color illumination using multiple LEDs which emit light at different colors.

* * * * *